United States Patent [19]

Bryson

[11] Patent Number: 4,664,312
[45] Date of Patent: May 12, 1987

[54] AIR FRESHENER DISPENSING APPARATUS

[75] Inventor: John D. Bryson, Milwaukee, Wis.

[73] Assignee: Vaportek, Inc., Milwaukee, Wis.

[21] Appl. No.: 806,490

[22] Filed: Dec. 9, 1985

[51] Int. Cl.$^4$ ............................................. A61L 9/12
[52] U.S. Cl. ..................................... 239/59; 206/0.5; 220/231; 222/561
[58] Field of Search .................................. 239/53–59; 222/559, 561; 206/0.5; 220/231

[56] References Cited

U.S. PATENT DOCUMENTS

| | | | |
|---|---|---|---|
| 2,765,194 | 10/1956 | Will | 239/59 |
| 3,506,168 | 4/1970 | Dowdy et al. | 222/561 X |
| 4,057,167 | 11/1977 | Lee | 222/559 X |
| 4,258,004 | 3/1981 | Valenzona et al. | 239/57 X |
| 4,285,441 | 8/1981 | Ziskind | 220/231 |

Primary Examiner—Andres Kashnikow
Attorney, Agent, or Firm—Michael, Best & Friedrich

[57] ABSTRACT

A dispensing apparatus comprising a container defining a chamber adapted to contain a substance to be dispensed into the atmosphere, the container including a first surface having therein a first opening communicating with the chamber, a plate member including a second surface and being secured to the container with the second surface facing and spaced from the first surface, and a valve plate including a second opening and being trapped between the first and second surfaces in sliding relation thereto for movement between a first position wherein the valve plate closes the first opening and a second position wherein the second opening is aligned with the first opening to permit the chamber to communicate with the atmosphere.

15 Claims, 12 Drawing Figures

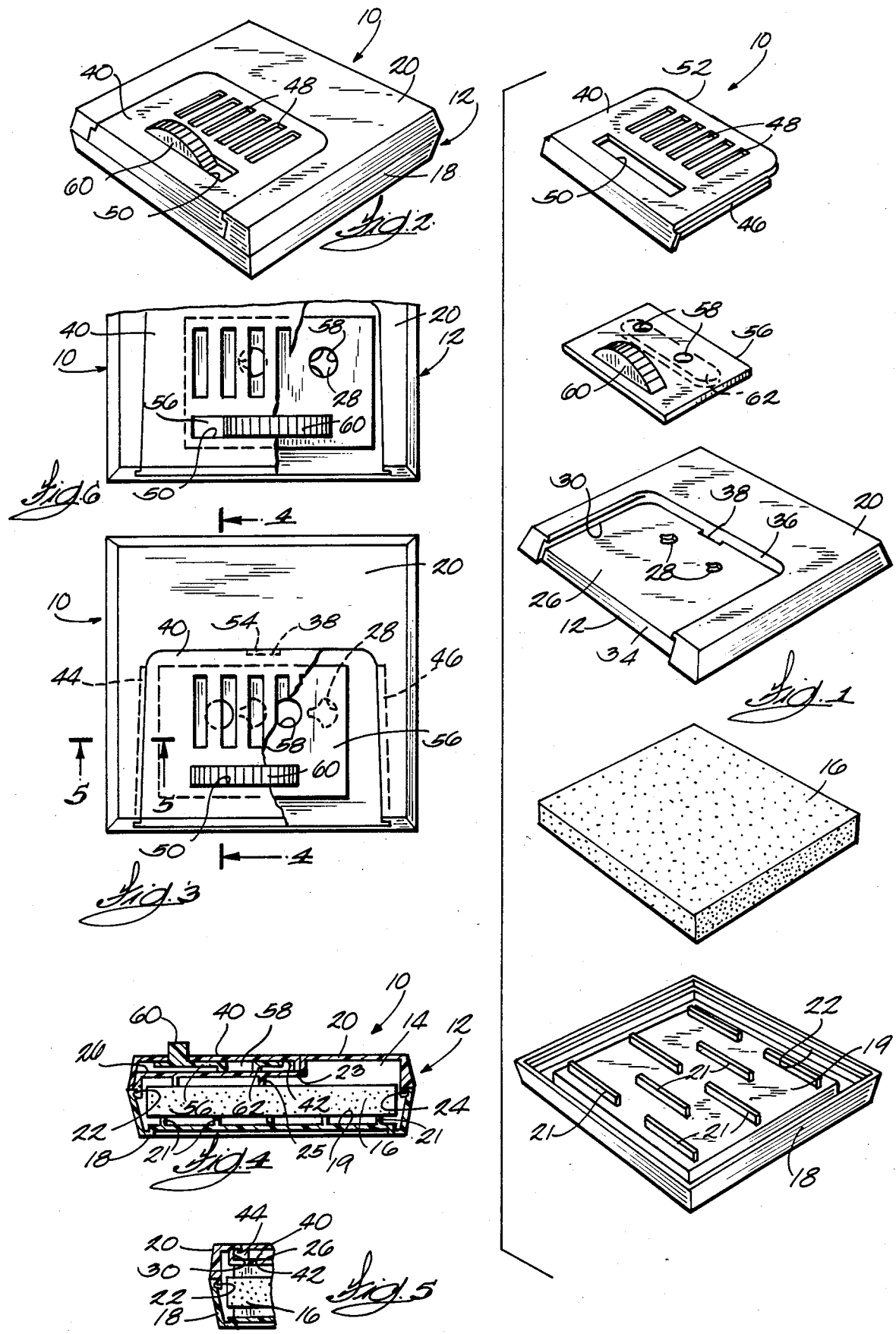

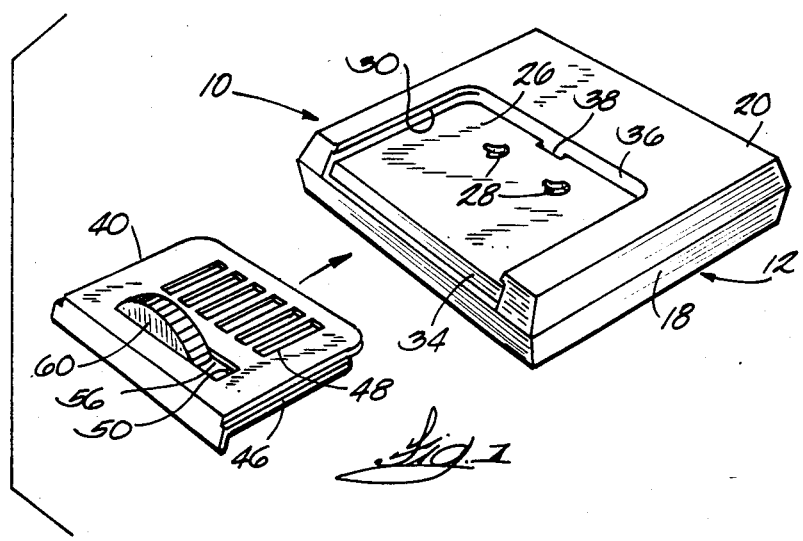
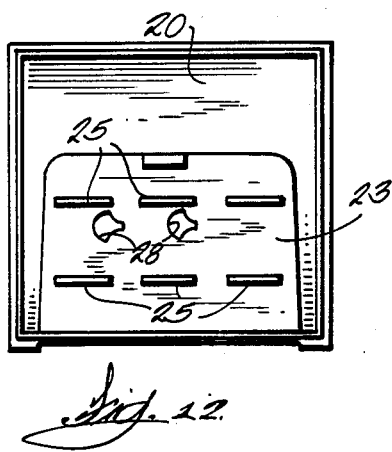
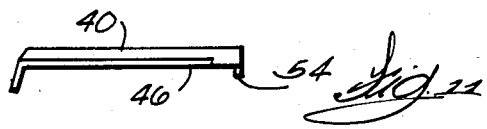
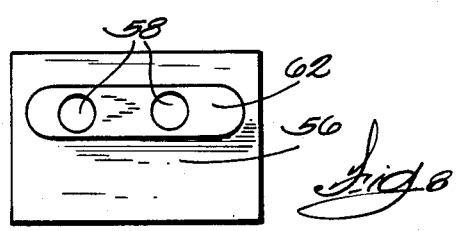
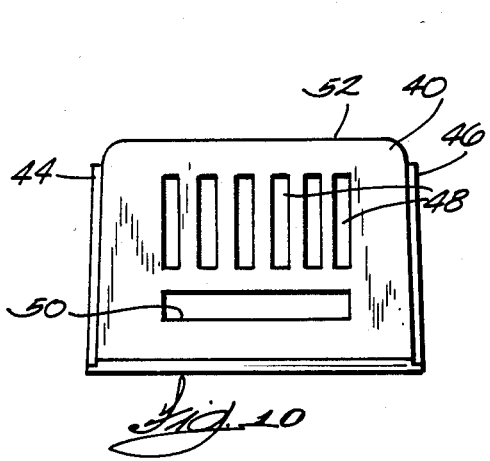
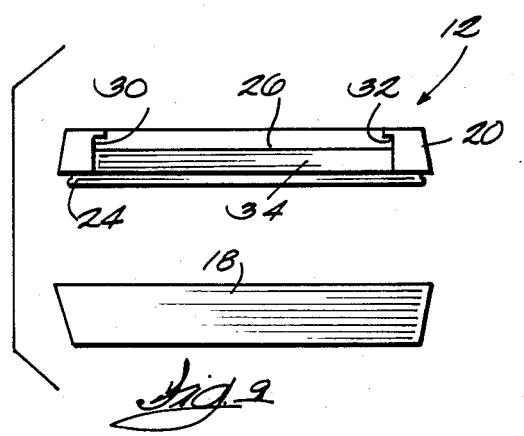

AIR FRESHENER DISPENSING APPARATUS

BACKGROUND OF THE INVENTION

The invention relates to dispensing apparatus, and more particularly to apparatus for dispensing air freshener or deodorant into the atmosphere.

SUMMARY OF THE INVENTION

The invention provides a dispensing apparatus comprising a container defining a chamber adapted to contain a package of a substance to be dispensed into the atmosphere, the container including a first surface having therein a first opening communicating with the chamber, the apparatus also comprising a plate member including a second surface, means for securing the plate member to the container with the second surface facing and spaced from the first surface, and a valve plate including a second opening and being trapped between the first and second surfaces in sliding relation thereto for movement between a first position wherein the valve plate closes the first opening and a second position wherein the second opening is aligned with the first opening to permit the chamber to communicate with the atmosphere.

In one embodiment, the apparatus further comprises means for constraining the valve plate to linear movement between the first and second positions.

In one embodiment, the plate member includes an elongated opening, and the valve plate includes a projection extending outwardly through the elongated opening and being adapted to be manually and reciprocally movable within the elongated opening so as to cause movement of the valve plate between the first and second positions.

In one embodiment, the apparatus further comprises means including the elongated opening and the aperture for constraining the valve plate to linear movement between the first and second positions.

In one embodiment, the plate member includes a grill portion partially covering the valve plate and aligned with the first opening to permit communication of the chamber with the atmosphere when the valve plate is in the second position.

In one embodiment, the means for securing the plate member to the container includes, in the container, a pair of opposed, generally parallel first and second slots located on opposite sides of the first surface and opening inwardly toward the first surface, and, on the plate member, opposite first and second flanges respectively slidably received in the first and second slots.

In one embodiment, the container further includes a stop surface extending between the slots and generally perpendicularly to the slots and to the first surface, and the plate member further includes an end surface extending generally perpendicularly to the first and second flanges and abutting the stop surface.

In one embodiment, the means for securing the plate member to the container further includes means for preventing disassembly of the plate member from the container.

In one embodiment, the means for preventing disassembly includes, in the first surface of the container, a recess located adjacent the stop surface, and, on the plate member, a resiliently deformable projection extending outwardly from the second surface and adjacent the end surface, the projection being received in the recess.

In one embodiment, the container includes a first portion having therein the first opening, and a second portion secured to the first portion.

In one embodiment, the first portion of the container has an inner surface partially defining the chamber and having thereon a plurality of outwardly extending ribs for supporting the substance away from the inner surface, and the second portion has an inner surface partially defining the chamber and facing the inner surface of the first portion, the inner surface of the second portion having thereon a plurality of outwardly extending ribs for supporting the substance away from the inner surface of the second portion.

The invention also provides a dispensing apparatus comprising a container defining a chamber adapted to contain a package of a substance to be dispensed into the atmosphere, the container including a first surface having therein a first opening communicating with the chamber, a pair of opposed, generally parallel first and second slots located on opposite sides of the first surface and opening inwardly toward the first surface, and a stop surface extending between the slots and generally perpendicularly to the slots and to the first surface, the first surface having therein a first opening communicating with the chamber, and a recess located adjacent the stop surface, a plate member having therein an elongated opening and including a second surface spaced from and facing the first surface, opposite first and second flanges respectively slidably received in the first and second slots, an end surface extending generally perpendicularly to the first and second flanges and abutting the stop surface, a resiliently deformable projection extending outwardly from the second surface and adjacent the end surface, the projection being received in the recess, and a grill portion aligned with the first opening, and a valve plate partially covered by the grill portion of the plate member and slidably trapped between said first and second surfaces, the valve plate including a second opening, and a second projection extending outwardly through the plate member elongated opening and being adapted to be reciprocally and manually movable within the elongated opening so as to cause linear movement of the valve plate between a first position wherein the valve plate closes the first opening and a second position wherein the second opening is aligned with the first opening to permit the chamber to communicate with the atmosphere through the first opening, the second opening, and the grill portion.

A principal feature of the invention is the above-described dispensing apparatus. The apparatus is simple to manufacture and to assemble.

Other principal features and advantages of the invention will become apparent to those skilled in the art upon review of the following detailed description, claims, and drawings.

DESCRIPTION OF THE DRAWINGS

FIG. 1 is an exploded view of a dispensing apparatus embodying the invention.

FIG. 2 is a perspective view of the dispensing apparatus.

FIG. 3 is a top view of the apparatus showing the valve plate in the closed position.

FIG. 4 is a cross-sectional view taken along line 4—4 in FIG. 3.

FIG. 5 is a cross-sectional view taken along line 5—5 in FIG. 3.

FIG. 6 is a partial top view of the apparatus showing the valve plate in the open position.

FIG. 7 is a partially exploded perspective view of the apparatus.

FIG. 8 is a bottom view of the valve plate.

FIG. 9 is an exploded front view of the container.

FIG. 10 is a top view of the plate member.

FIG. 11 is a side view of the plate member.

FIG. 12 is a bottom view of the upper portion of the apparatus.

Before one embodiment of the invention is explained in detail, it is to be understood that the invention is not limited in its application to the details of construction and the arrangements of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

DESCRIPTION OF THE PREFERRED EMBODIMENT

A dispensing apparatus 10 embodying the invention is illustrated in the drawings. Preferably, the entire dispensing apparatus 10 is made of plastic, although any suitable material can be employed. Also, the various components of the apparatus 10 need not all be made of the same material.

The apparatus 10 comprises a generally square container 12 defining a chamber 14 (FIG. 4) adapted to contain a package 16 of a substance, preferably an air freshener or a deodorant, to be dispensed into the atmosphere. In the preferred embodiment, the container 12 includes a lower portion 18, and an upper portion 20 connected to the lower portion 18. In the illustrated construction, the lower portion 18 has (see FIG. 1) an inner or upper surface 19 partially defining the chamber 14 and having thereon a plurality of outwardly extending ribs 21 for supporting the package 16 away from the surface 19, and the upper portion 20 has (see FIGS. 4 and 12) an inner or lower surface 23 partially defining the chamber 14 and facing the upper surface 19. The lower surface 23 has thereon a plurality of outwardly extending ribs 25 for supporting the package 16 away from the surface 23. The ribs 21 and 25 prevent the package 16 from contacting the surfaces 19 and 23, respectively, so as to allow air flow over substantially the entire surface of the package 16.

While the upper and lower portions 20 and 18, respectively, of the container 12 can be connected in any suitable manner, in the illustrated construction, the lower portion 18 includes an inner surface having therein an endless groove 22 (FIGS. 1, 4 and 5), and the upper portion 20 includes an outer surface having thereon a peripherally extending projection 24 (FIGS. 4 and 9) snapped into the groove 22.

The upper portion 20 of the container 12 includes a first or upper surface 26 having therein one or more first openings 28 communicating with the chamber 14, and a pair of opposed, generally parallel first and second slots 30 and 32, respectively, (FIGS. 1, 5, 7 and 9) located on opposite sides of the upper surface 26 and opening inwardly toward the upper surface 26. Preferably, the upper portion 20 of the container 12 includes an outer edge 34 (FIGS. 1 and 7), and the first and second slots 30 and 32 extend inwardly from the outer edge 34. In the preferred embodiment, as best shown in FIG. 3, the first and second slots 30 and 32 are not exactly parallel, but converge slightly as they extend inwardly from the outer edge 34 of the container 12. The upper portion 20 of the container 12 also includes (see FIGS. 1 and 7) a stop surface 36 extending between the first and second slots 30 and 32 and generally perpendicularly to the slots 30 and 32 and to the upper surface 26. In the preferred embodiment, the upper surface 26 has therein a recess 38 located adjacent the stop surface 36.

If desired, the container 12 can also include adhesive means (not shown) on the lower portion 18 to permit attachment of the container 12 to a mounting surface.

The apparatus 10 also comprises a plate member 40 including an underside defining a second or lower surface 42 (FIGS. 4 and 5), and means for securing the plate member 40 to the upper portion 20 of the container 12 with the lower surface 42 facing and spaced from the upper surface 26 of the container 12.

In the preferred embodiment, the plate member 40 includes (see FIG. 10) opposite first and second outward extensions or flanges 44 and 46 respectively slidably received in the first and second slots 30 and 32 of the container 12. The first and second flanges 44 and 46 of the plate member 40 preferably converge as do the first and second slots 30 and 32. For reasons explained hereinafter, in the preferred embodiment, the plate member 40 further includes an elongated opening 50, and a grill portion 48. For reasons also explained hereinafter, the grill portion 48 is aligned with the first openings 28 of the container 12. In the preferred embodiment, the plate member 40 further includes an end surface 52 extending generally perpendicularly to the first and second flanges 44 and 46. The plate member 40 preferably further includes a resiliently deformable projection 54 extending outwardly from the lower surface 42 and adjacent the end surface 52, the projection 54 being received in the recess 38 in the upper surface 26 of the container 12.

While various suitable means for securing the plate member 40 to the container 12 can be employed, in the preferred embodiment, such securing means includes the plate member flanges 44 and 46 and the container slots 30 and 32. Preferably, the securing means further includes means for preventing disassembly of the plate member 40 from the container 12. While various suitable means for preventing disassembly can be used, in the preferred embodiment, such means includes the plate member projection 54 and the container recess 38. The plate member 40 is secured to the container by sliding the first and second flanges 44 and 46 into the first and second slots 30 and 32, as shown in FIG. 7, until the end surface 52 of the plate member 40 abuts the stop surface 36 of the container 12 and the projection 54 is inserted into the recess 38.

The apparatus 10 further comprises a valve plate 56 including one or more second openings 58 corresponding to respective ones of the first openings 28. The valve plate 56 is trapped between the lower surface 42 of the plate member 40 and the upper surface 26 of the container 12 in sliding relation thereto for movement between a first or closed position (FIG. 3) wherein the valve plate 56 closes the first openings 28 and a second or open position (FIG. 6) wherein the second openings 58 are aligned with the first openings 28 to permit the chamber 14 to communicate with the atmosphere. In the preferred embodiment, the valve plate 56 is partially covered by the grill portion 48 of the plate member 40. Because the grill portion 48 is aligned with the first openings 28 of the container 12, when the valve plate 56 is in the open position, the chamber 14 communicates with the atmosphere through the first openings 28, the second openings 58, and the grill portion 48.

In the preferred embodiment, the apparatus 10 further comprises means for constraining the valve plate 56 to linear movement between the first and second positions. While various suitable constraining means can be employed, in the preferred embodiment, the valve plate 56 includes a second projection 60 which extends outwardly through the elongated opening 50 and which is adapted to be manually and reciprocally movable within the elongated opening 50 so as to cause movement of the valve plate 56 between the first and second positions, and the constraining means includes the elongated opening 50 and the projection 60. In the illustrated construction, the projection 60 has thereon a plurality of ridges to facilitate manual movement of the projection 60 and therefore of the valve plate 56.

As best shown in FIGS. 4 and 8, in the preferred embodiment, the valve plate 56 has an underside which faces the upper surface 26 of the container 12 and which has thereon a raised portion 62 surrounding the second openings 58. The raised portion 62 substantially ensures contact of the underside of the valve plate 56 with the upper surface 26 of the container 12 adjacent the first openings 28, thereby substantially ensuring sealing or closing of the first openings 28 when the valve plate 56 is in the closed position.

Various other features and advantages of the invention are set forth in the following claims.

I claim:

1. A dispensing apparatus comprising a container defining a chamber adapted to contain a substance to be dispensed into the atmosphere, said container including a first surface having therein a first opening communicating with said chamber, said apparatus also comprising a plate member including a second surface, means for assembling said plate member to said container by moving said plate member in a first plane and along a first path relative to said container and with said second surface facing and spaced from said first surface, and a valve plate including a second opening and being trapped between said first and second surfaces in sliding relation thereto for movement in a second plane parallel to and spaced from said first plane and along a second path transverse to said first path and between a first position wherein said valve plate closes said first opening and a second position wherein said second opening is aligned with said first opening to permit said chamber to communicate with the atmosphere.

2. A dispensing apparatus as set forth in claim 1 and further comprising means for constraining said valve plate to linear movement between said first and second positions.

3. A dispensing apparatus as set forth in claim 1 wherein said plate member includes an elongated opening, and wherein said valve plate includes a projection extending outwardly through said elongated opening and being adapted to be manually and reciprocally movable within said elongated opening so as to cause movement of said valve plate between said first and second positions.

4. A dispensing apparatus as set forth in claim 3 and further comprising means including said elongated opening and said aperture for constraining said valve plate to linear movement between said first and second positions.

5. A dispensing apparatus as set forth in claim 1 wherein said plate member includes a grill portion partially covering said valve plate and aligned with said first opening to permit communication of said chamber with the atmosphere when said valve plate is in said second position.

6. A dispensing apparatus as set forth in claim 1 wherein said container includes a side edge, wherein said means for assembling said plate member to said container includes, in said container, a pair of opposed, generally parallel first and second slots open at said side edge and located in facing relation on opposite sides of said first surface, and, on said plate member, opposite first and second flanges respectively slidably received in said first and second slots.

7. A dispensing apparatus as set forth in claim 6 wherein said container further includes a stop surface intermediate said slots and generally perpendicularly to said slots and to said first surface, and wherein said plate member further includes an end surface extending generally perpendicularly to said first and second flanges and abutting said stop surface.

8. A dispensing apparatus as set forth in claim 7 wherein said means for assembling said plate member to said container further includes means for preventing disassembly of said plate member from said container.

9. A dispensing apparatus as set forth in claim 8 wherein said means for preventing disassembly includes, in said first surface of said container, a recess located adjacent said stop surface, and, on said plate member, a resiliently deformable projection extending outwardly from said second surface and adjacent said end surface, said projection being received in said recess.

10. A dispensing apparatus as set forth in claim 1 wherein said means for assembling said plate member to said container further includes means for preventing disassembly of said plate member from said container.

11. A dispensing apparatus as set forth in claim 1 wherein said container includes a first portion having therein said first opening, and a second portion secured to said first portion.

12. A dispensing apparatus as set forth in claim 11 wherein said first portion of said container has an inner surface partially defining said chamber and having thereon a plurality of outwardly extending ribs for supporting the substance away from said inner surface, and wherein said second portion has an inner surface partially defining said chamber and facing said inner surface of said first portion, said inner surface of said second portion having thereon a plurality of outwardly extending ribs for supporting the substance away from said inner surface of said second portion.

13. A dispensing apparatus comprising a container defining a chamber adapted to contain a substance to be dispensed into the atmosphere, said container including a first surface, a pair of opposed, generally parallel first and second slots located on opposite sides of said first surface and opening inwardly toward said first surface, and a stop surface intermediate said slots and generally perpendicularly to said slots and to said first surface, said first surface having therein a first opening communicating with said chamber, and a recess located adjacent said stop surface, a plate member having therein an elongated opening with a dimension transverse to said slots and including a second surface spaced from and facing said first surface, opposite first and second flanges respectively slidably received in said first and second slots, an end surface extending generally perpendicularly to said first and second flanges and abutting said stop surface, a resiliently deformable projection extending outwardly from said second surface and adjacent said end surface, said projection being received in said recess, and a grill portion aligned with said first opening, and a valve plate partially covered by said grill portion of said plate member and slidably trapped between said first and second surfaces, said valve plate including a second opening, and a second projection extending outwardly through said plate member elongated opening and being adapted to be reciprocally and manually movable within said elongated opening so as to cause linear movement of said valve plate along a apth transverse to said slots and between a first position wherein said valve plate closes said first opening and a second position wherein said second opening is aligned with said first opening to permit said chamber to communicate with the atmosphere through said first opening, said second opening, and said grill portion.

14. A dispensing apparatus as set forth in claim 13 wherein said container includes a first portion having therein said first opening, and a second portion secured to said first portion.

15. A dispensing apparatus as set forth in claim 14 wherein said first portion of said container has an inner surface partially defining said chamber and having thereon a plurality of outwardly extending ribs for supporting the substance away from said inner surface, and wherein said second portion has an inner surface partially defining said chamber and facing said inner surface of said first portion, said inner surface of said second portion having thereon plurality of outwardly extending ribs for supporting the substance away from said inner surface of said second portion.

* * * * *